United States Patent
Duma

(10) Patent No.: US 9,198,597 B2
(45) Date of Patent: Dec. 1, 2015

(54) LEADING-EDGE CANCER TREATMENT

(75) Inventor: Christopher Duma, Newport Beach, CA (US)

(73) Assignee: Christopher Duma, Newport Beach, CA (US)

( * ) Notice: Subject to any disclaimer, the term of this patent is extended or adjusted under 35 U.S.C. 154(b) by 778 days.

(21) Appl. No.: 12/471,294

(22) Filed: May 22, 2009

(65) Prior Publication Data

US 2010/0014637 A1  Jan. 21, 2010

Related U.S. Application Data

(60) Provisional application No. 61/055,437, filed on May 22, 2008.

(51) Int. Cl.
| | |
|---|---|
| *A61B 5/05* | (2006.01) |
| *A61B 5/055* | (2006.01) |
| *G01R 33/465* | (2006.01) |
| *A61N 5/10* | (2006.01) |

(52) U.S. Cl.
CPC .............. *A61B 5/055* (2013.01); *G01R 33/465* (2013.01); *A61N 5/10* (2013.01)

(58) Field of Classification Search
USPC ................. 600/407, 410, 411, 417, 437; 324/306–309
See application file for complete search history.

(56) References Cited

U.S. PATENT DOCUMENTS

| | | | | |
|---|---|---|---|---|
| 4,955,365 | A | * | 9/1990 | Fry et al. ............................ 601/2 |
| 5,579,766 | A | * | 12/1996 | Gray .............................. 600/407 |
| 2006/0029580 | A1 | * | 2/2006 | Yu et al. ........................ 424/93.7 |
| 2006/0052690 | A1 | * | 3/2006 | Sirohey et al. ................. 600/420 |
| 2006/0173378 | A1 | * | 8/2006 | Fonss .............................. 600/578 |
| 2006/0177378 | A1 | * | 8/2006 | Norfray .......................... 424/9.3 |
| 2006/0264713 | A1 | * | 11/2006 | Pedain et al. .................. 600/300 |
| 2007/0208074 | A1 | * | 9/2007 | Bonni et al. ................... 514/449 |
| 2007/0219174 | A1 | * | 9/2007 | Miller et al. .................. 514/185 |
| 2007/0225553 | A1 | * | 9/2007 | Shahidi ......................... 600/103 |
| 2008/0292160 | A1 | * | 11/2008 | Raghavan et al. ............. 382/128 |
| 2009/0221675 | A1 | * | 9/2009 | Graf Matuschka Von Greiffenclau ............... 514/44 A |

OTHER PUBLICATIONS (Dissemination and Growth of Cancer Cells in Metastatic Sites, 2002 nature publishing group, vol. 2, Aug. 2002, 563).*
Duma, Christopher, slide presentation, entitled "Essential Tremor," 17 pages, Oct. 27, 2001.
Duma, Christopher, et al., slide presentation, entitled "The Role of MRI and Proton MRS in Directing 'Leading Edge' Boost Gamma Knife Radiosurgery for Recurrent Glioblastoma Multiforme," 36 pages, May 2004.

(Continued)

*Primary Examiner* — Amanda Lauritzen Moher
*Assistant Examiner* — Shahdeep Mohammed
(74) *Attorney, Agent, or Firm* — Knobbe Martens Olson & Bear LLP

(57) ABSTRACT

Kits and methods for the treatment of certain types of cancers, specifically various primary brain cancers. In some embodiments, treatment is directed toward the known areas of cancer cell infiltration and along pathways of likely migration ahead of established areas of cancer cell infiltration. In some embodiments, cancer cells are targeted where they have likely spread, but yet remain undetected. Some embodiments relate to a means of automatically directing radiological analysis along likely pathways of cancer cell migration to precisely determine the extent of detectable cancer spread. In some embodiments, treatments are directed to a predetermined distance along such pathways.

14 Claims, 19 Drawing Sheets

(56) References Cited

OTHER PUBLICATIONS

Duma, Christopher, et al., slide presentation, entitled "Radiosurgical Boost Treatment of 'The Leading Tumor Edge' in Patients with Glioblastoma Multiforme: A Trend Toward Improved Outcome," 17 pages, Jun. 8, 2001.

Duma, Christopher, et al., slide presentation, entitled "Rationale for and Results of a 6-Year Experience of 'Leading Edge' Gamma Knife Radiosurgery for Glioblastoma Multiforme: A Trend Toward Improved Outcome," 51 pages, Mar. 2005.

Duma, Christopher, slide presentation, entitled "GBM is a Local Disease: Rationale for 'Leading Edge' Radiosurgery," 91 pages, May 13, 2005.

Duma, Christopher, slide presentation, entitled "Modern Brain Surgery," 81 pages, Mar. 12, 2002.

Duma, Christopher, slide presentation, entitled "Modern Brain Surgery," 83 pages, Oct. 18, 2001.

Duma, Christopher, slide presentation, entitled "Gamma Knife Brain Surgery: An 11-Year Experience," 88 pages, Oct. 11, 2001.

Duma, Christopher, slide presentation, entitled "Modern Brain Tumor Surgery," 83 pages, May 6, 2003.

Duma, Christopher, slide presentation, entitled "Image-Guided Brain Surgery Immunotherapy," 68 pages, Jan. 2003.

Duma, Christopher, slide presentation, entitled "Gamma Knife Program *The First 5½ Years*," 81 pages, Feb. 2003.

Duma, Christopher, slide presentation, entitled "Modern Stereotactic Radiosurgery: Tools, Tricks and Complication Avoidance," 93 pages, Sep. 2003.

\* cited by examiner

LEADING-EDGE CANCER TREATMENT

BACKGROUND OF THE INVENTION

1. Field of the Invention

The present disclosure relates to a method for the diagnosis and treatment of certain types of cancer, especially various types of malignant brain tumors.

2. Description of the Related Art

Glial cell tumors are the most common types of primary brain cancers. They are classified by grade and cell type. The main cell types involved are astrocytes, ependymal cells, and oliodendrocytes. There are four grades of astrocytomas. Grade I and II are "low-grade" gliomas and Grade III and IV are "high-grade" gliomas. While low-grade gliomas are characterized by differentiated cells and are benign, high-grade gliomas are characterized by undifferentiated cells and are malignant.

Glioblastoma multiforme (GBM), or Grade IV astrocytoma, constitutes the most commonly diagnosed and most malignant type of primary brain tumor, affecting 8,000-12,000 new patients per year, or roughly 40% of all patients newly diagnosed with primary brain tumors. GBM is a progressive disease such that even after diagnosis and resection of the cancer cells in the early grades of the disease, degradation to its higher grades has heretofore proven unavoidable and local treatment options have proven unsatisfactory. Computed tomographic (CT) scans and magnetic resonance imaging (MRI) are the primary non-invasive tools for diagnosing GBM.

The median life expectancy for patients with GBM is three to six months without treatment. Current treatment options include the surgical resection of the bulk of the tumor, radiotherapy with involved-field radiation therapy (IFXRT), and chemotherapy. While resection can delay the spread of low-grade gliomas, some GBM cells typically remain undetected outside the treatment area and survive the procedure. As these cells multiply and spread, new tumors typically appear about a centimeter outside the resection cavity. With radiation therapy, the median life expectancy of GBM patients is about a year. Photon radiation augmented with temozolomide chemotherapy is known to add two to three months to the median life expectancy. Given the dismal prognosis associated with GBM, there is clearly a need for more effective means of treating this illness.

SUMMARY OF THE INVENTION

Disclosed herein is a method of treating various types of cancer, specifically the use of targeted radiotherapy directed at likely pathways of migration for cancer cells. Some embodiments herein disclosed are particularly useful for the treatment various types of brain cancers such as GMB. In some embodiments, the bulk of the tumor, or nidus, is detected radiographically. Likely pathways of migration for the cancer cells are then determined based on the location of the nidus. These pathways are further analyzed to determine if cancer cells have already migrated thereto. In addition to surgically excising and/or irradiating known areas of tumor infiltration, treatments can also be directed toward these likely pathways ahead of the leading edge of verified cancer cell migration. In this manner, those cancer cells that have migrated the farthest from the nidus, yet still remain undetectable because of their small number, can be inactivated or destroyed by specifically directing radiation treatments to their suspected location. This technique enables the practitioner to maximize the number of tumor cells eliminated using the lowest possible dosage of radiation, thereby minimizing the iatrogenic destruction of healthy brain tissue. This enables the practitioner to eliminate suspected, yet undetectable cancer cells that would otherwise multiply and spread to other parts of the brain.

In some embodiments, the present disclosure can comprise a kit further comprising a data processing and storage device, one or more imaging devices, and one or more treatment devices. Said data processing and storage device can further comprise software or other executable code capable of determining likely areas of cancer cell migration based on an analysis of the tumor nidus and direct additional radiological analysis thereto. These areas of likely cancer cell infiltration can be determined through an analysis of established areas of cancer cell infiltration and a determination of those pathways along which cancer cells preferentially migrate. Once the verified leading edge of cancer cell migration is determined, the likely location of yet undetected cells can be determined with reference to known migratory patterns as well as other information about the patient's type of cancer. In some embodiments, the kit can further comprise an executable code capable of directing treatments at the known and likely areas of cancer cell infiltration based on previously gathered radiological data. In many cases, the executable code can comprise various commands for delivering appropriate treatments in the areas of likely cancer cell infiltration so as to maximize treatment effect.

DETAILED DESCRIPTION OF THE PREFERRED EMBODIMENT

Figure 1:
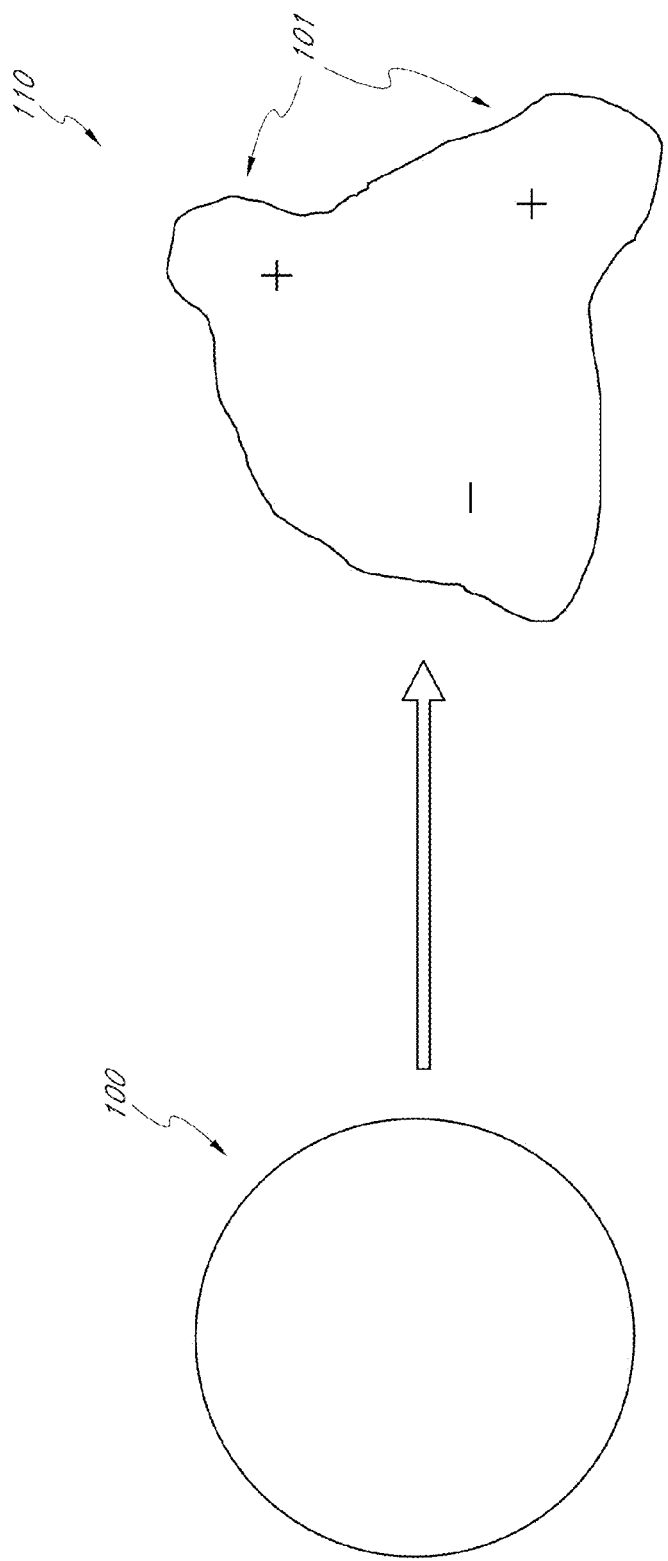
FIG. 1 is an illustration of the transformation of a healthy cell into a cancer cell.
Figure 2:
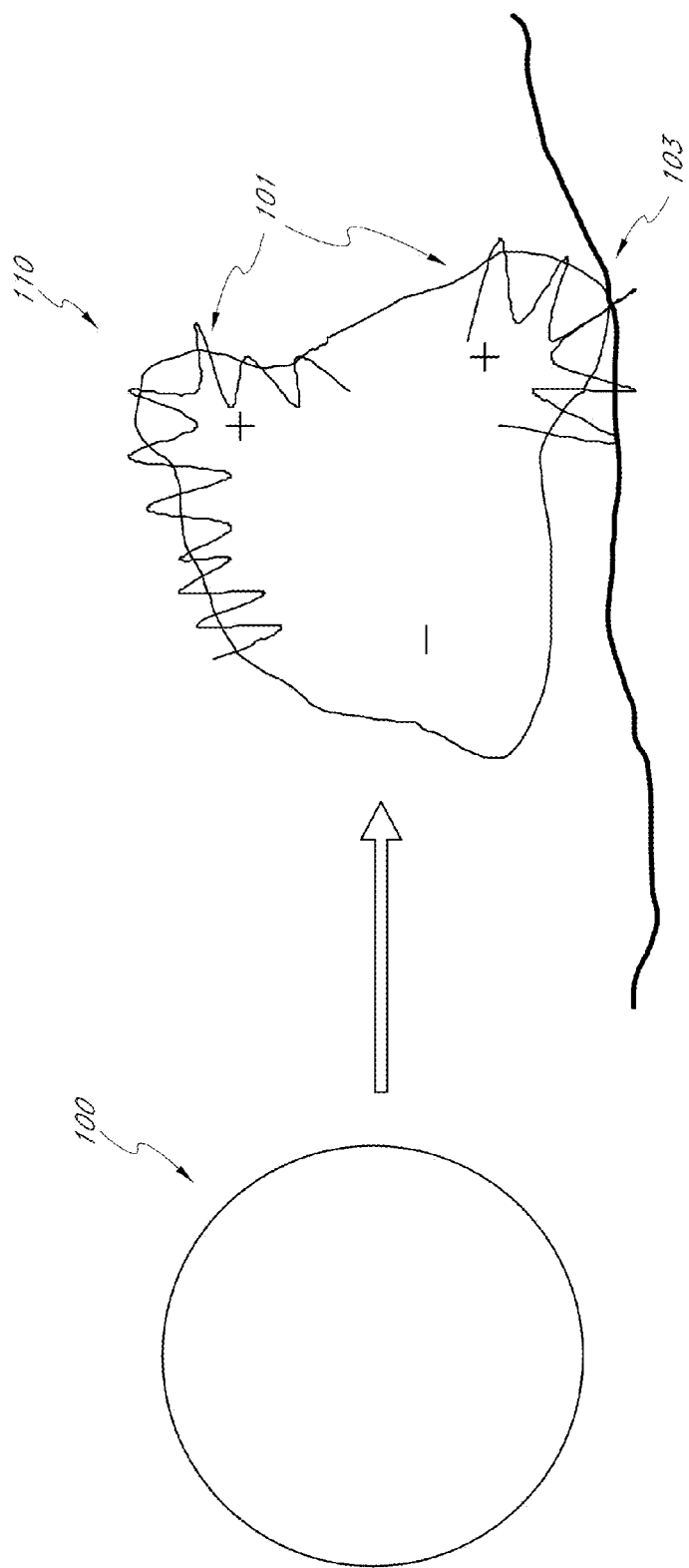
FIG. 2 is an illustration of a cancer cell developing actin and signaling proteins that enable it to interact with the extracellular matrix.
Figure 3:
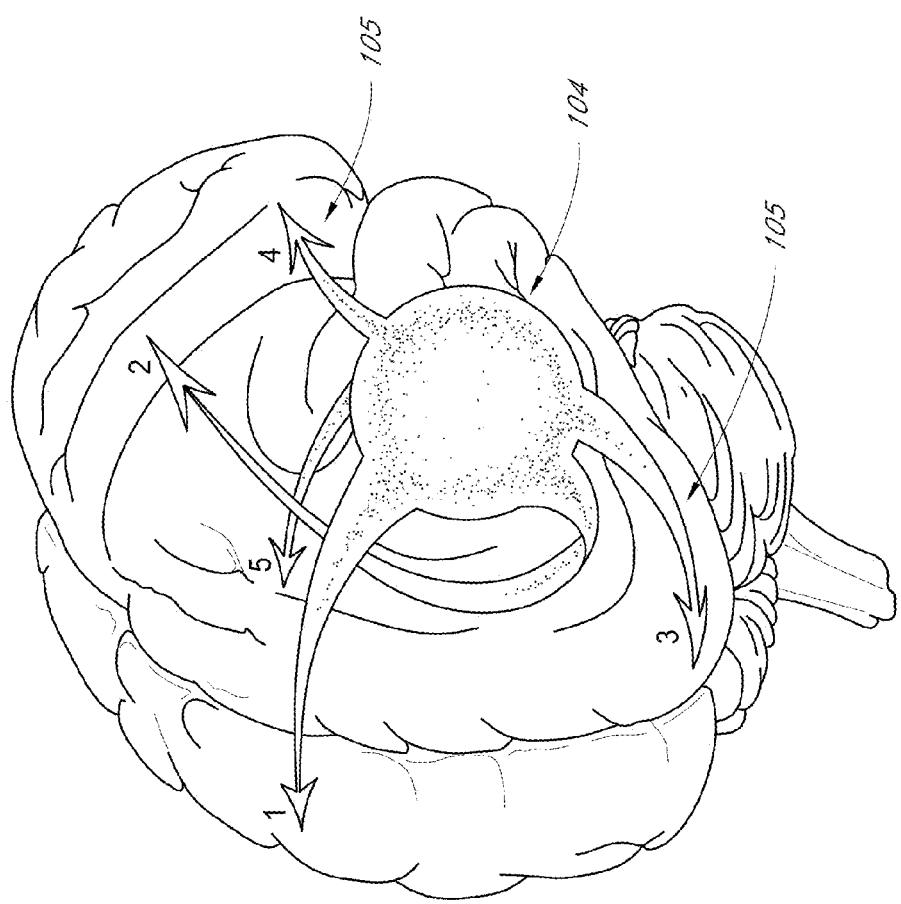
FIG. 3 is an illustration of the spread of cancer cells from a nidus to other parts of the brain.
Figure 4A:
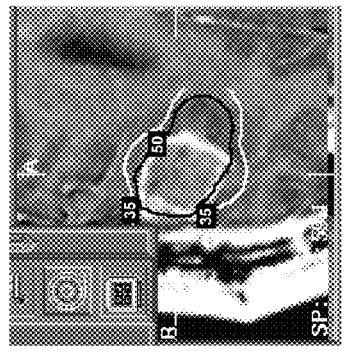
FIGS. 4A to 4H are a series of eight radiographic images of a brain during treatment for GBM.
Figure 4B:
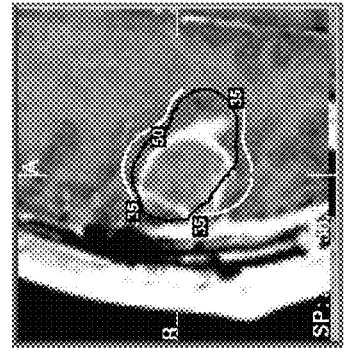
Figure 4C:
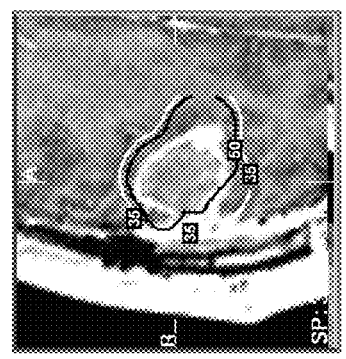
Figure 4D:
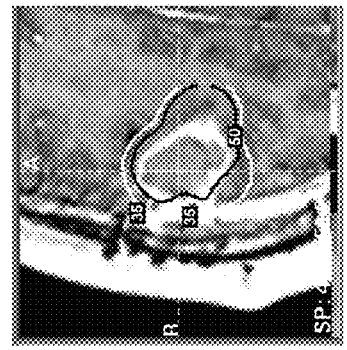
Figure 4E:
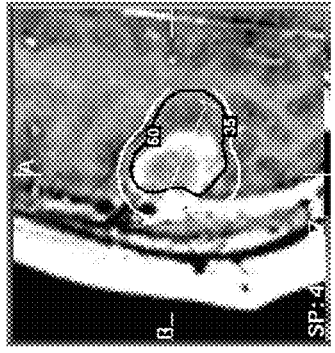
Figure 4F:
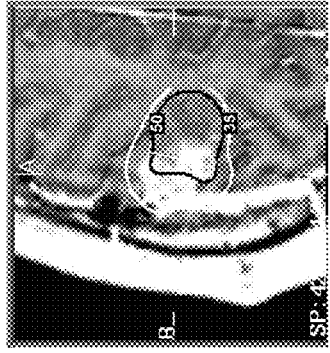
Figure 4G:
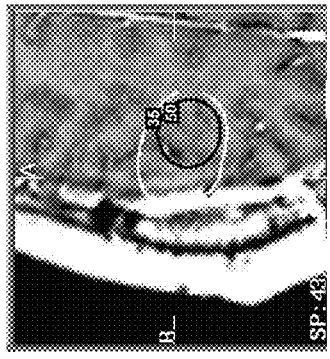
Figure 4H:
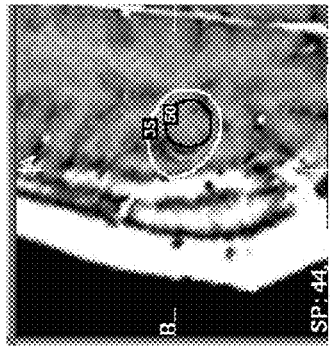
Figure 4J:
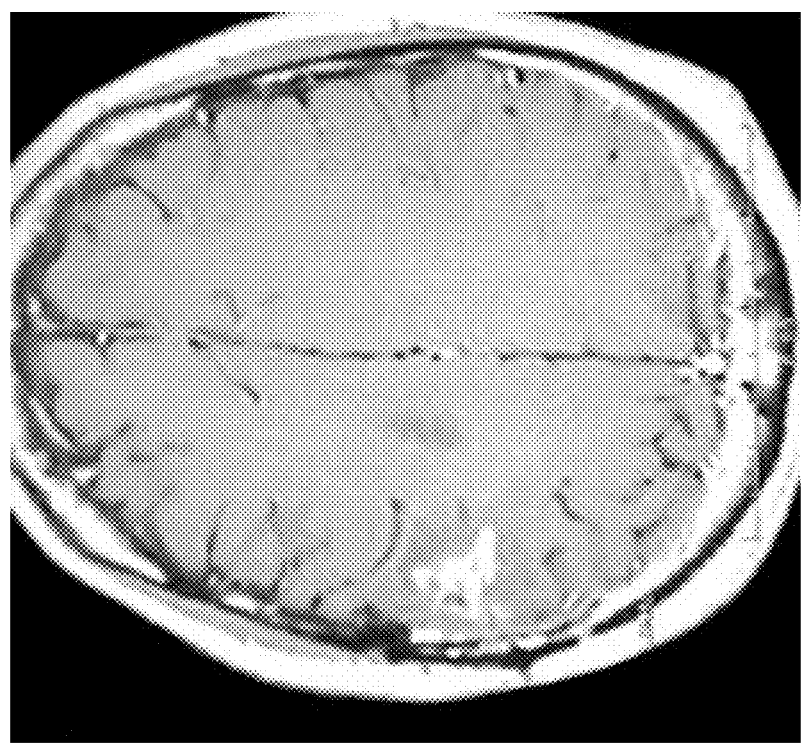
FIG. 4J shows a radiographic image of the same brain after treatment.
Figure 8:
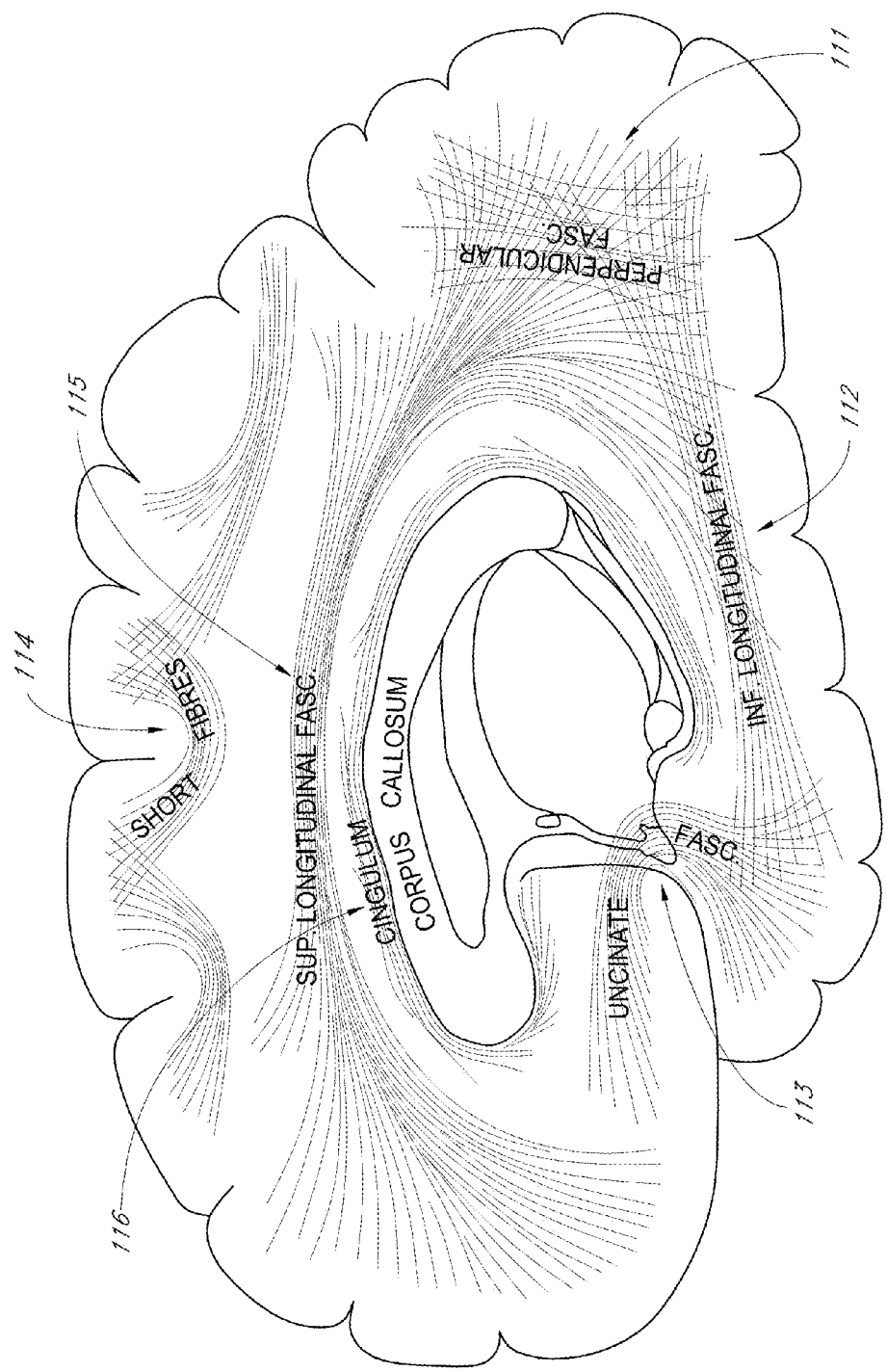
FIG. 8 is an illustration of various white matter pathways in the brain.
Figure 9:
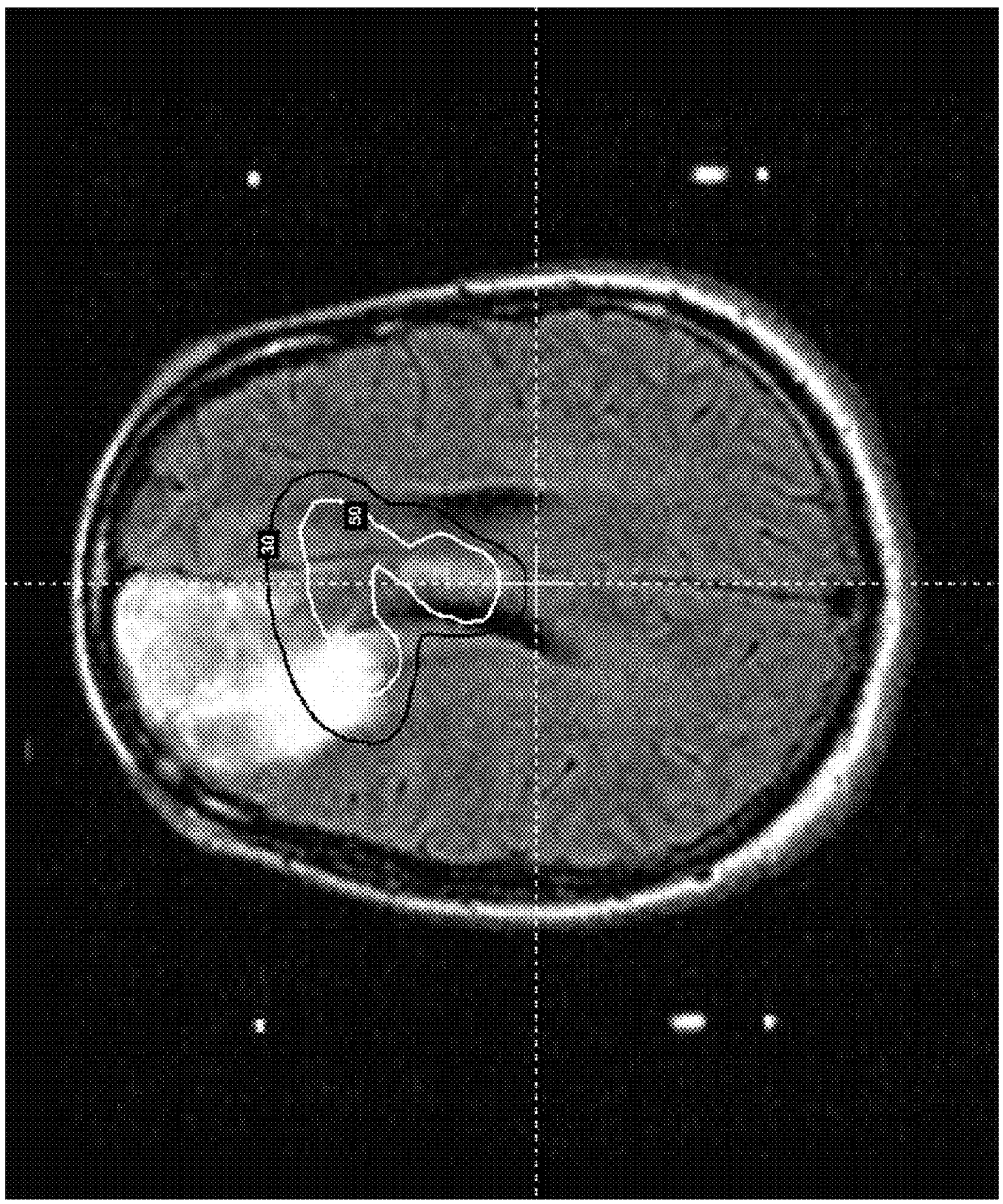
FIGS. 9-15 depict various radiation treatment profiles in accord with the present disclosure.
Figure 10:
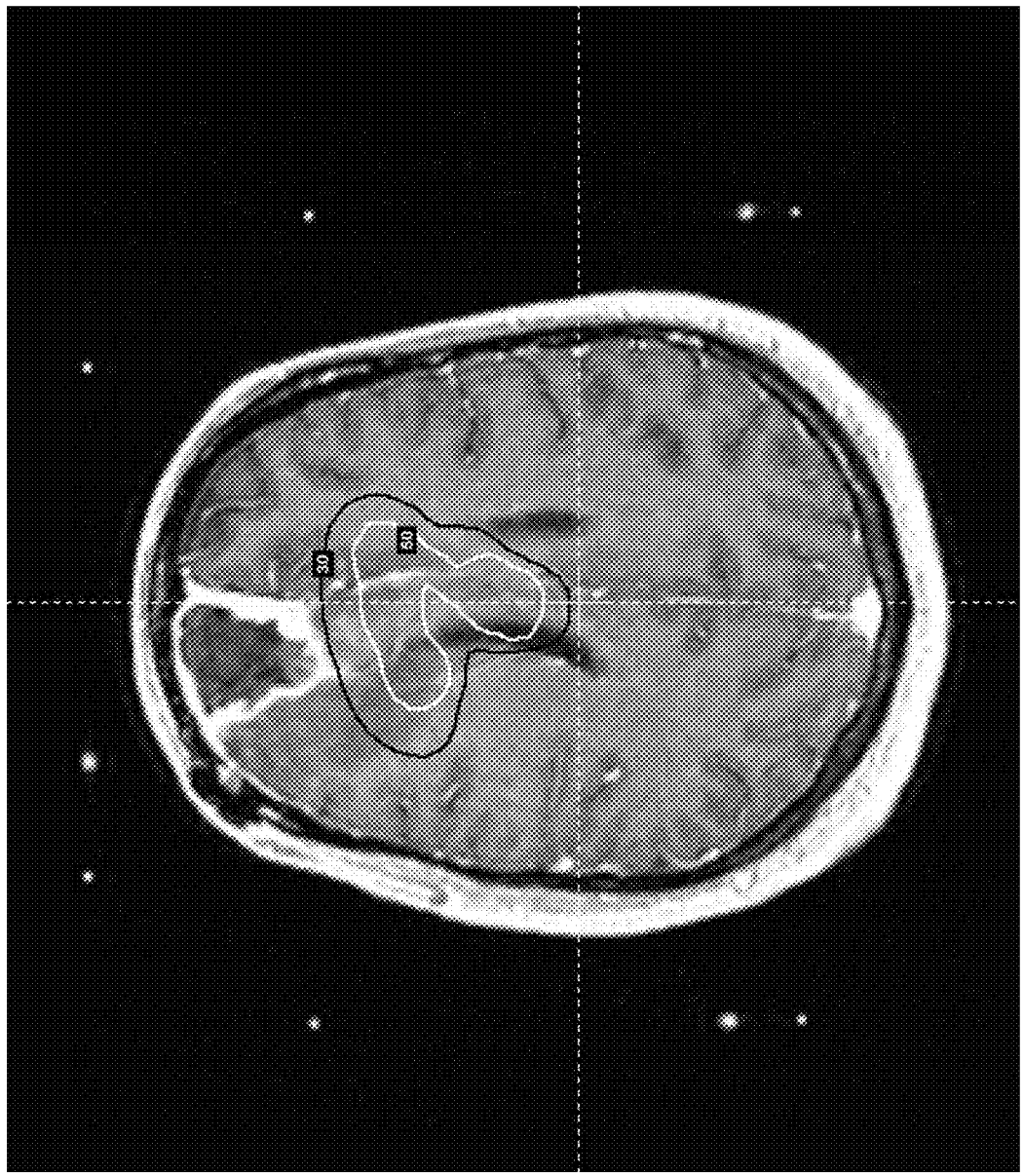
Figure 11:
Figure 12:
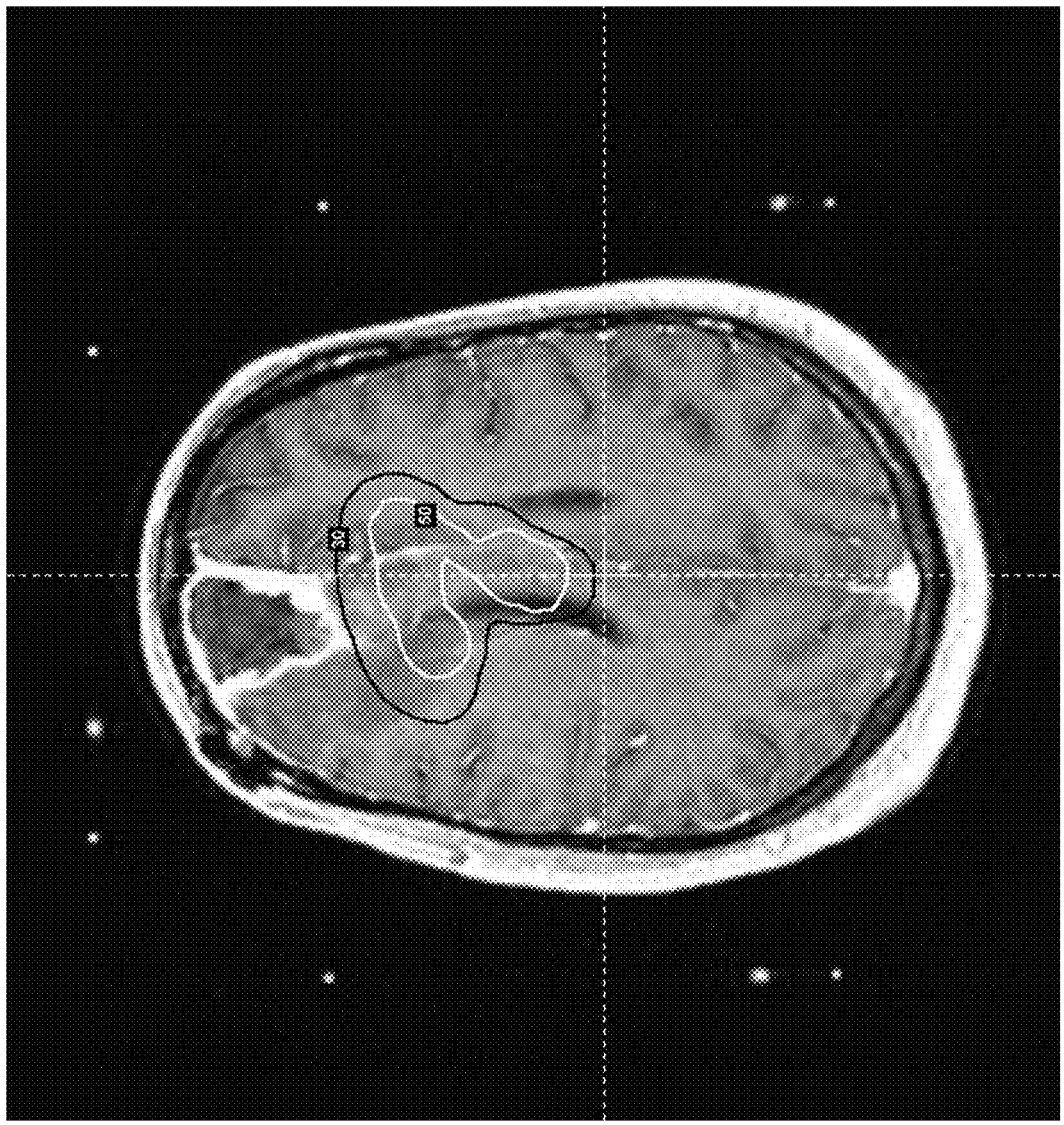
Figure 13:
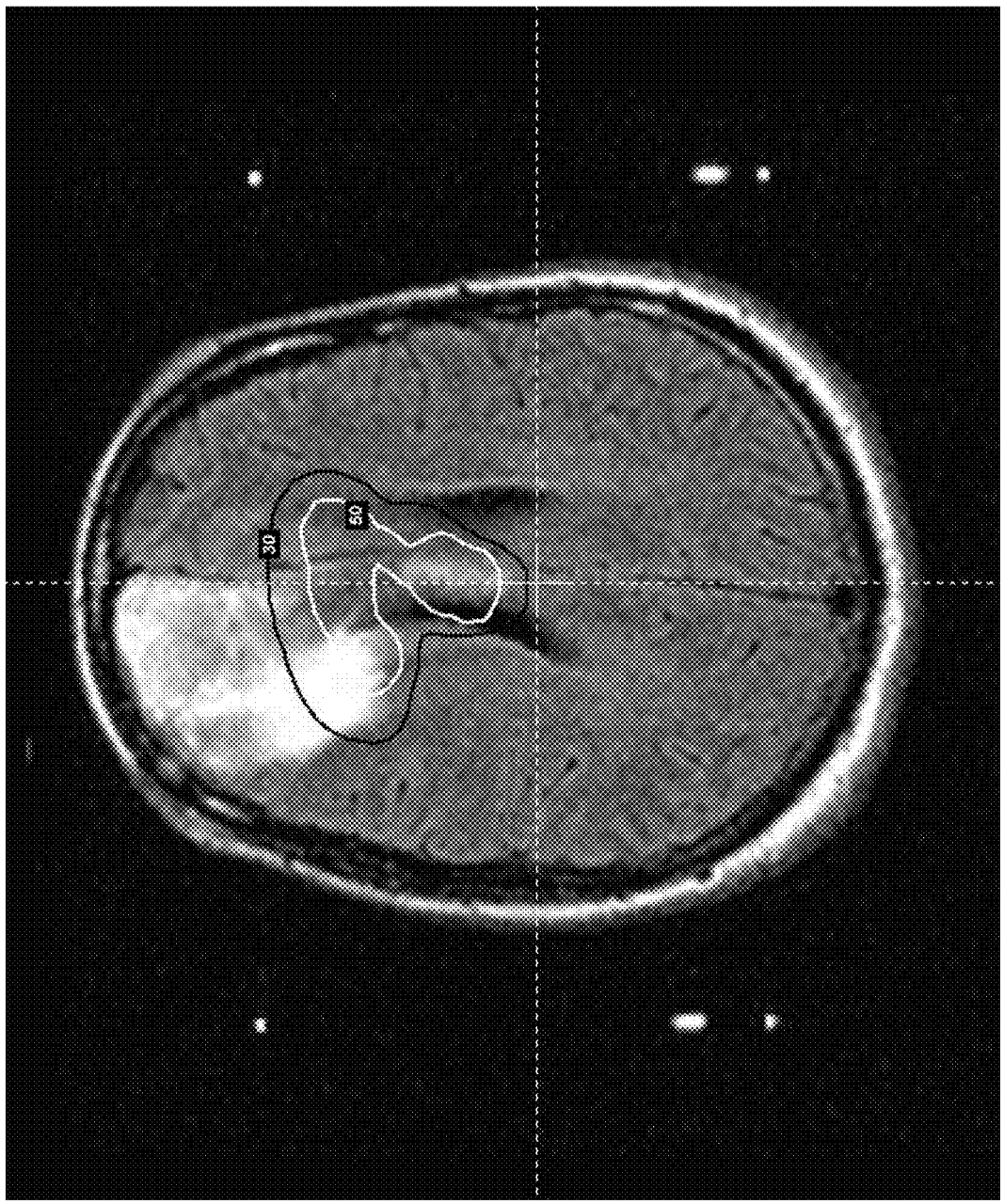
Figure 14:
Figure 15:
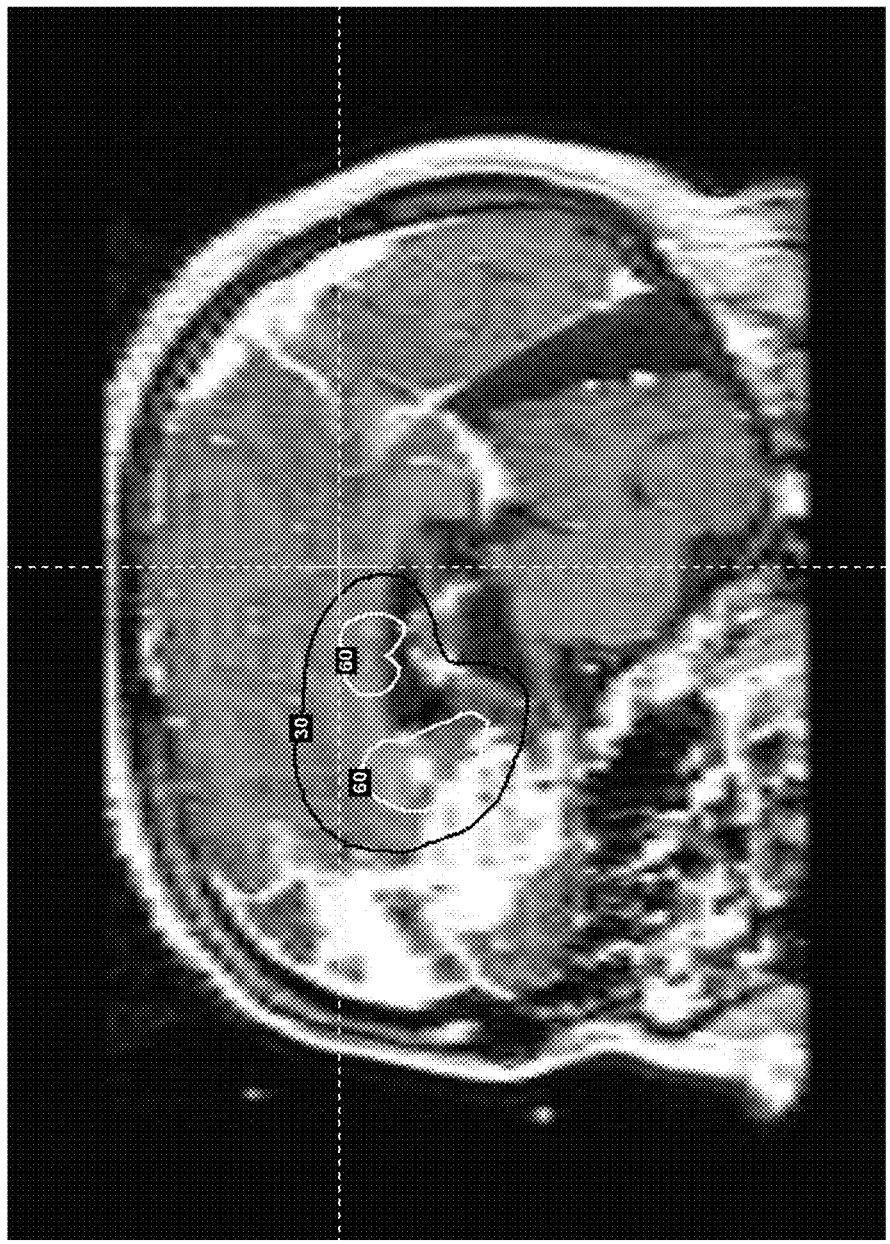

The present disclosure relates to methods of diagnosing and treating various types of cancer. Some embodiments are specifically directed to the treatment of patients with primary brain cancers such as GBM. Some embodiments arise from a recognition that cancer cells from the nidus can migrate to other portions of the brain as a result of the loss of normal inhibitory controls and changes in cell morphology. As depicted in FIGS. 1 and 2, cancer cells 100 undergo a number of changes resulting in the development of a motile phenotype 110. These mutated cells are characterized by the polarization of the cell and the development of pseudopodia and/or invadopodia 101 that the cancer cell 110 can use for mobility. In addition, said cancer cells 110 can deploy actin and various signaling proteins 102 on their surface membranes that enable them to interact with the extracellular matrix 103 so as to facilitate their ability to migrate. As illustrated in FIG. 3, cancer cells migrate from a central nidus 104 to other parts of the brain in predictable patterns following various defined pathways 105. These pathways comprise various white matter tracts in the brain on which cancer cells preferentially migrate. Some known pathways are depicted in FIG. 8. Treatment by applying a dose or doses of stereotactic radiation to the tissue most likely to migrate and/or the path along which such migration is most likely to take place ("leading-edge" surgery) is effective. FIGS. 4A through 4H shows a series of radiographic images of the brain of a 39 year-old patient with GBM taken during treatment with involved field radiotherapy (IFXRT) using this technique. FIG. 4J is a radiographic image of the same patient's brain seven years after treatment was completed. Given that the American Cancer Society estimates the five year survival rate of a GBM patient of this age is about 13% with conventional treatment, the treatment in this case was clearly effective.

Some disclosed embodiments relate to methods for gathering data to identify an optimal treatment area or areas in portions of the brain such that a command or series of commands can be formulated, generated, and input into a treatment device or a control element thereof. These commands can then direct radiotherapy or other treatments to specific locations along the likely pathways of cancer cell migration based on the location of the location of the nidus.

Some embodiments relate to methods of treatment planning whereby brain tissue regions are identified for treatment. Such regions can correspond to what are believed to be the leading-edges of cancer cell migration. This is sometimes referred to herein as a "leading-edge target." In some embodiments, Fluid-Attenuated Inversion-Recovery (FLAIR) sequences provide data that indicate the location or regions of potentially cancerous tissue. This can be used to identify the leading-edge migration of cancer cells could arise and/or to identify a leading-edge target. FLAIR images are advantageous because their enhanced image quality over other methods allows detection of smaller regions of cancer cells remote from the nidus, however it is conceivable that other techniques could result in suitable images.

Figure 5:
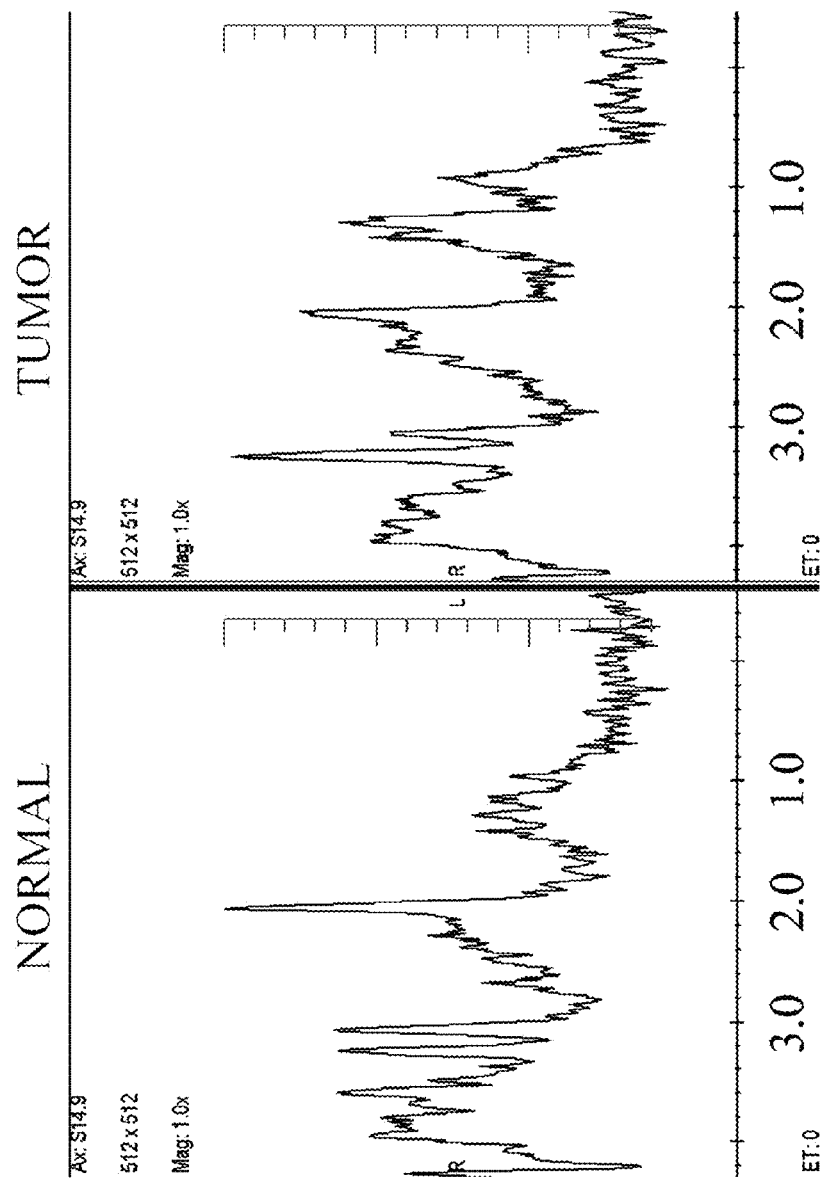
FIG. 5 is shows magnetic resonance spectrograms of tissues.

In some embodiments, Magnetic Resonance Spectroscopy (MRS) can be used to determine the leading-edge target by providing data on the composition of brain tissue that lies outside a region of documented tumor spread. MRS spectra can differentiate between non-target regions (e.g., unaffected tissue or necrotic regions) and areas infiltrated by cancer cells. FIG. 5 shows how MRS spectra vary depending on whether the examined brain cells are normal or cancerous.

FIG. 8 illustrates some of the white matter pathways in the brain along which cancer cells preferentially migrate. A partial list of the depicted pathways includes the perpendicular fasciculus 111, uncinate fasciculus 113, superior longitudinal fasciculus 115, and cingulum 116. However, a variety of other white matter tracts that can facilitate cancer cell migration including the corona radiata, internal capsule, arcuate and occipito-temporal fasciculi, etc. Based on the location of the nidus in relation to these pathways, MRS can be applied to create spectra corresponding to a voxel, or three dimensional region, near the perimeter of the nidus, focusing on those pathways wherein malignant cells are understood to migrate.

Figure 6A:
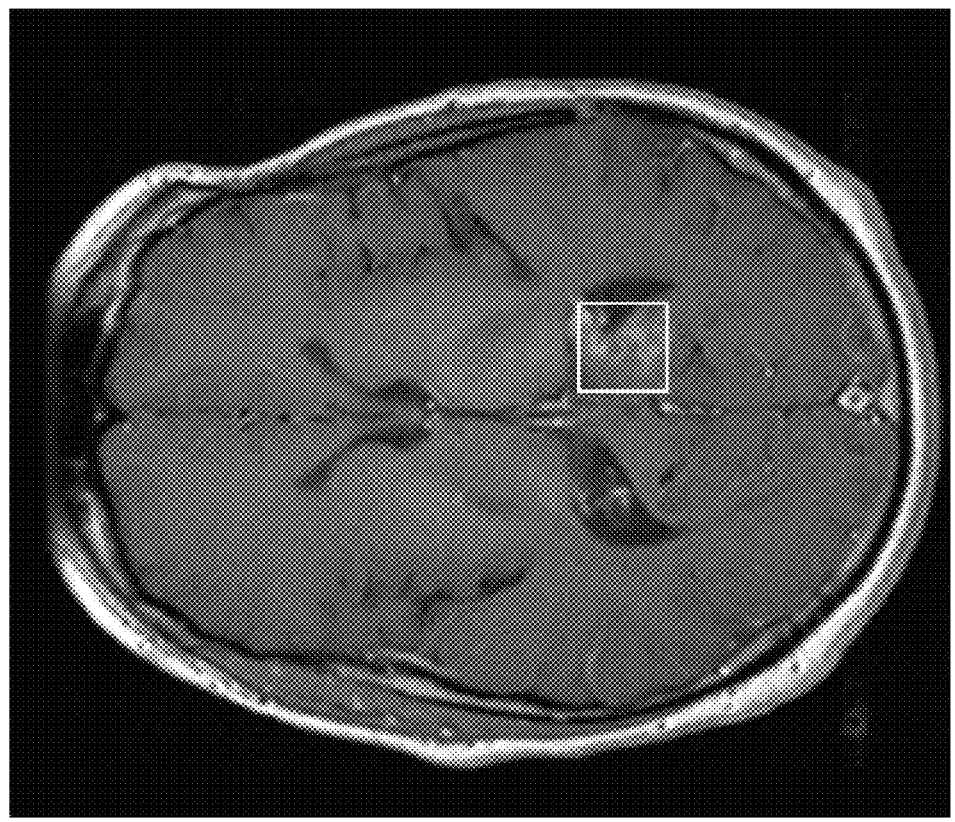
FIGS. 6A and 6B are an example of a single voxel-array with the corresponding magnetic resonance spectrogram.
Figure 6B:
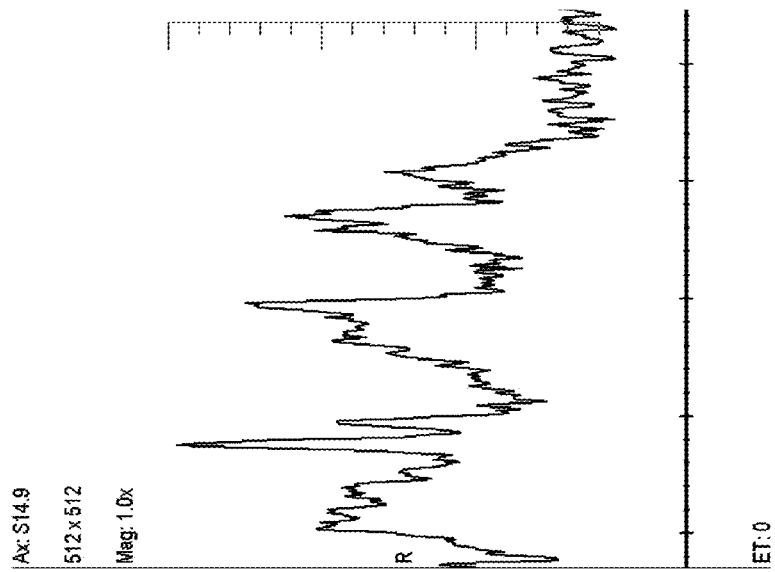
Figure 7B:
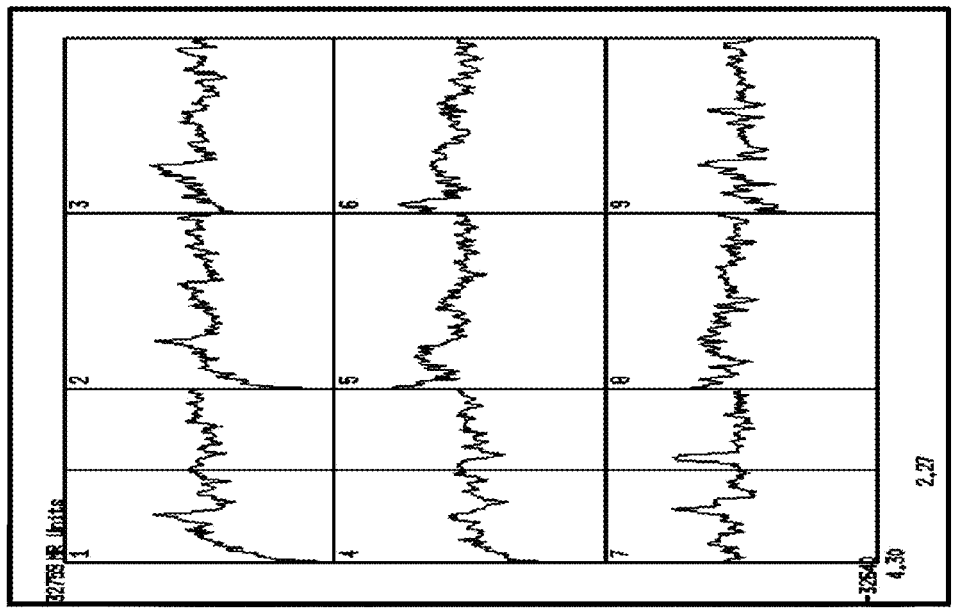
FIGS. 7A and 7B are an example of a multi voxel-array.
Figure 7A:
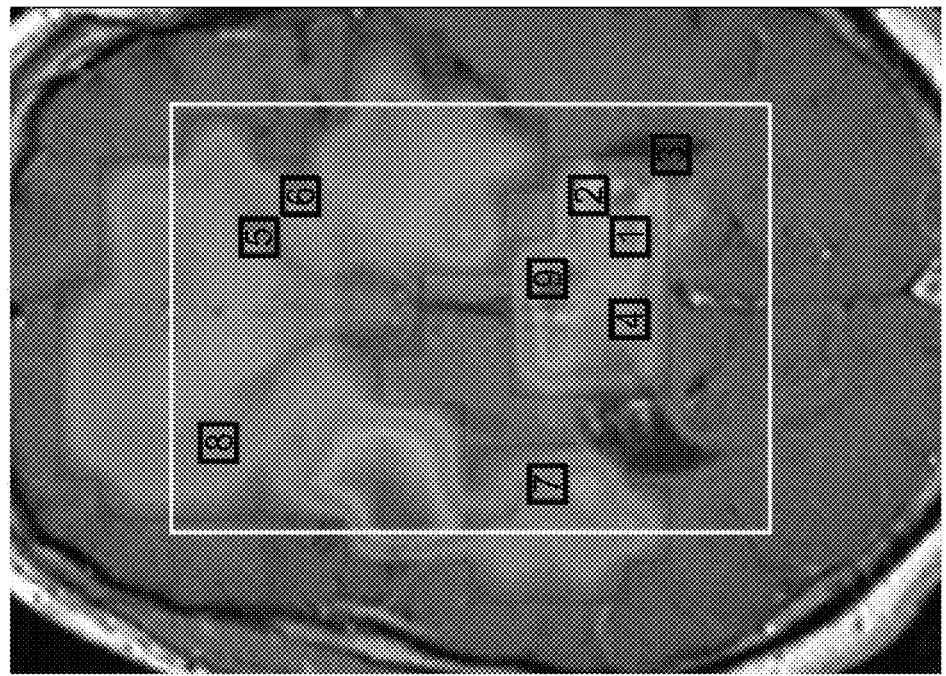

FIG. 6A shows an example of a single voxel on a CT scan. FIG. 6B shows the corresponding MRS data for the voxel. In many embodiments, a series of voxel-arrays, or multiple-voxel-arrays with the corresponding MRS analysis can be performed. FIGS. 7A and 7B show an example of such a multiple-voxel-array. One, two, or multiple-voxel-arrays can be employed separately or in combination. MRS can also be used on a second or expanded first voxel-array to further analyze one or more leading-edge pathways along which the cells could potentially migrate. MRS spectra fitting a profile corresponding to cancer cells can be used to identify leading-edge targets.

Stereotactic radiosurgery constitutes one way in which brain cancers can be treated. This technique employs the use of an array of radiation beams targeted to converge on a single point or region within the body. This technique allows minimally-invasive intervention because it is not necessary to cut or otherwise damage a pathway through healthy tissue in order to apply treatment to site of the tumor. While the individual beams of radiation may travel through tissue, the dosage of radiation is insignificant except in the immediate region of convergence wherein radiation levels are sufficiently intense to damage the DNA and constituent proteins of the target tissue. The damaged cells in the targeted area may die or be sufficiently injured so that they are unable to replicate. However, the surrounding tissue is largely unaffected by the minimal amounts of radiation passing through in route to the site of convergence.

Gamma Knife radiosurgery (GKRS) is a method of stereotactic radiosurgery that utilizes a Gamma Knife. In some embodiments, GKRS is performed on tumor regions. In some embodiments, tumor regions are identified with MRS and/or FLAIR techniques as described herein. In some embodiments, treatment isodose plans based on MRS data can be prescribed to treat tissue regions that correspond to MRS and/or FLAIR signal abnormalities. In some embodiments, IFXRT is administered before leading-edge GKRS treatment. In some embodiments, leading-edge treatment is administered in conjunction with chemotherapy and/or immunotherapy. Stereotactic radiosurgery may be administered by other radiation tools such as the Cyberknife, Tomotherapy, linear accelerator (linac) machines, or other devices for which this technique would also be applicable.

Figure 18:
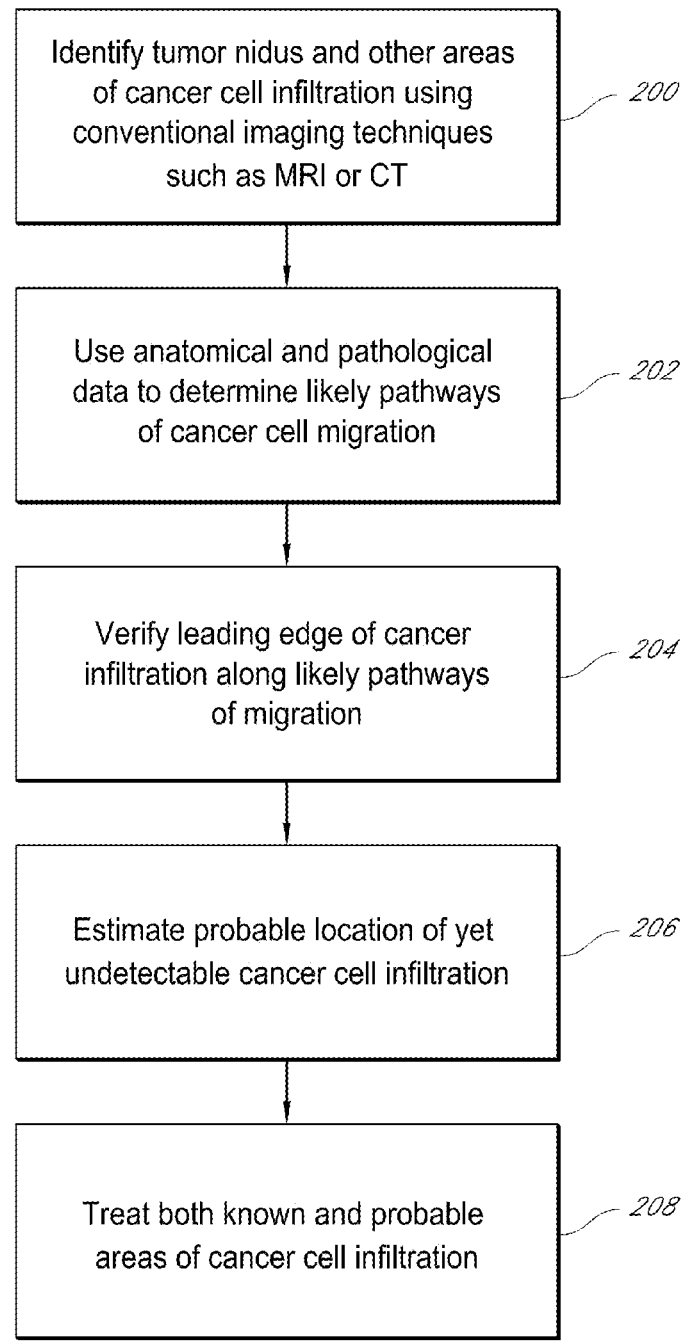
FIG. 18 is a flowchart depicting some of the steps involved in planning and executing leading-edge cancer treatment.

Some embodiments of leading-edge cancer treatment can be used in the treatment of GBM or other primary brain cancers. The method can involve planning a treatment of brain tissue that is remote from a concentration of cancer cells, e.g., a nidus. A representation of the steps involved in this treatment method is depicted in FIG. 18. First, an area that is infiltrated or highly concentrated with cancer cells is identified 200. Cancer cells are also located that are remote from the identified area of highly-concentrated cancer cells 200. As discussed below, any suitable method or device for identifying or locating cancer cells, including remote cancer cells, can be used. In some embodiments, such methods include conventional devices such as CT or MRI imaging can be used. One technique for locating remote cancer cells comprises first obtaining one or more FLAIR images of the brain to detect areas containing cancer cells. In some embodiments, upon locating brain tissue that is likely to contain cancer cells 202, a further confirmation of the nature of the cells is performed 204. For example, an array of MRS spectra is collected along potential routes of migration, e.g., white matter pathways and/or in regions surrounding the areas identified with reference to the FLAIR images. The MRS spectra can be analyzed to determine the extent of cancer cell migration beyond the cancerous region detected in the FLAIR images.

The MRS spectra also can be analyzed to determine the nature of the cells detected in the FLAIR images. In some embodiments, Voxels in the MRS-array that indicate tumor cells are used as reference to guide a trajectory for targeted radiation into the probably location of undetectable cancerous cells 206. In some embodiments, FIGS. 6 and 7 depict the use of voxels in this manner. In some embodiments, the specific areas selected for MRS analysis can include the white matter pathways depicted in FIG. 8 and other likely routes of likely cancer cell migration 208.

Once the treatment targets have been identified, these areas may be treated and the cancer cells therein destroyed 208. In some embodiments, this can involve the use of stereotactic radiotherapy delivered using a Gamma Knife or similar device. This device can be programmed to trace out a particular trajectory and deliver specified doses of radiation along this trajectory. Such trajectories can have irregular or regular three dimensional shapes within the brain tissue. This treatment can be directed at the nidus or other known areas to which the cancer cells have spread. However, in some embodiments, the treatment can also be along one or more preferred cancer cell migration pathways such as the white matter tracts depicted in FIG. 8. In some cases, this treatment can be directed at sites of likely, but yet undetected cancer cell migration along these or other tracts.

Some embodiments of the present disclosure further comprise a kit comprising a processing device configured to analyze data from medical imaging devices, formulate treatment protocols based on said data, as well as control and monitor various stereotactic treatment devices to execute an appropriate treatment plan. This kit can further comprise software or other executable code provided on a computer-readable medium of data-storage device. In some embodiments, the commands are provided on a computer-readable medium that can be updated and/or supplemented based on experimental or diagnostic findings or history. In some embodiments, the commands are stored on a device and broadcast as signals from that device or another device.

In some embodiments, said kit comprises a computer processor or other device capable of executing algorithms or commanding a separate device to execute algorithms that identify for an operator or help an operator identify potential target tissue based on imaging data. As discussed in greater detail herein, any source of imaging data that can identify a target for leading-edge treatment can be used. Some examples include FLAIR sequences and/or single or multiple voxel MRS.

In some embodiments, a kit includes software of an executable code loaded onto at least one computer-readable medium and/or devices. The executable code can include modules that can be operated by a computer processor to instruct imaging and/or treatment devices to perform methods of some embodiments. The computer readable storage medium can be any suitable permanent or temporary storage medium. For example, a compact disc, a CD-ROM, RAM, a flash drive, a hard drive, one or more hard drives stored at a remote location, etc.

The executable code can take any suitable form, but preferably includes modules that facilitate at least one of the methods discussed herein. For example, the executable code can include a module for controlling the imaging of tissues. The control provided by the imaging control module can include complete control of a device that generates an image showing or representing tissue or can include just high level commands as to specific image to capture. For example, the imaging control module can be configured with a plurality of commands to obtain images of the nidus or other region or regions of origin of cancer and a plurality of pathways of potential cancer cell migration.

The executable code can also include a module for confirming the nature of the cells in any of the images captured by the imaging control module. The tissue confirmation module can, for example, include one or more commands for controlling a tissue characterizing device, such as a command to operate a spectroscopic instrument, for example, an instrument for generating FLAIR images, a command to load an image or to load signal data corresponding to an image into a device capable of executing an algorithm for analyzing that data, a command to export the results of that analysis to a microprocessor which determines based on preset criteria whether further images should be gathered or whether a proper characterization has been made with the already available images. Thus, for example, the tissue confirmation module can be configured to collect and analyze data useful in distinguishing areas of non-cancerous tissue from areas of cancerous tissue.

In some embodiments, the executable code can include a leading-edge pathway identification module adapted to locate areas of potential or actual propagation of cancer cells. For example, the leading-edge pathway identification module could perform all of the steps discussed above with respect to the imaging control module. Additionally, the leading-edge pathway identification module could perform similar steps of collecting and evaluating image or signal data corresponding to an image as discussed above with respect to spectral or voxel-arrays.

In some embodiments, a kit includes an atlas or other indication showing, listing, or describing a set of brain regions known or believed to be particularly suitable for or susceptible to migration of cancer cells. For example, in one embodiment a kit includes an atlas of potential pathways along which cancer cells (e.g., GBM) could move. As discussed in greater detail herein, such potential pathways could be exploited by such cancer cells as they migrate from the nidus. The inventor has discovered that focusing a suitable treatment based on knowledge and imaging of these pathways can prevent or minimize propagation of cancer cells along these "leading-edge" pathways, thereby preventing or minimizing spread of such cells within the brain. The potential pathway can include white matter pathways, which are regions along which tumors preferentially migrate. In some embodiments, the set of regions (e.g., an atlas) can be manually or automatically updated with additional information. In some embodiments, an atlas can be manually updated with additional information. In some embodiments, an atlas can be automatically updated with additional information. In some embodiments, an atlas is self-updating based on single or multiple patient or patient-group histories. This data can include information specific to the patient's cancer and/or general data on the patient's type of cancer based on various research or statistical data. The patient or patient-group histories may include data obtained in various places throughout the world and transferred to a device, which is included in some embodiments, for storage or further transfer or information processing including data integration.

In some embodiments, the kit includes a device capable of analyzing FLAIR and MRS images, through, for example, pattern recognition, to prescribe a treatment, such as a region to be radiated or an amount of radiation to be applied or both. One or more aspects of the embodiments disclosed herein can be performed or located remotely from other aspects of the embodiments, such that analysis and treatment can be performed in locations that are remote from each other. Communication between components can be by any suitable means, e.g., wired communication, secured- or unsecured-wireless communication, over the Internet or private network, etc.

In some embodiments, the executable code can include a module for prescribing a treatment for a tissue region remote from an area of cancer cell concentration. The treatment prescription module can take any suitable form, such as defining a stereotactic treatment regimen for applying a suitable dose of radiation to an area remote from an area of initial cancer cell concentration or formation.

In some embodiments, a kit includes a device adapted to provide commands for directing a Gamma Knife or other stereotactic device capable of administering treatments. These commands can include treatment coordinates and/or radiation dosing instructions. In some embodiments, the kit further includes one or more devices capable of administering isodoses of radiation.

In some embodiments, the treatment prescription module is also adapted to actually control a radiation delivery apparatus, such as a Gamma Knife or other stereotactic apparatus. In other embodiments, the treatment prescription module provides inputs to a controller of such a device. For example, the treatment prescription module can be configured to generate a plurality of coordinates defining a region for treatment at a tissue location, e.g., at a region of tissue remote from a nidus. The coordinates can define a complex geometry of tissue and, thus, can circumscribe complex multi-dimensional structures, such as masses of tumor and/or pathways of cancer cell migration.

Figure 16:
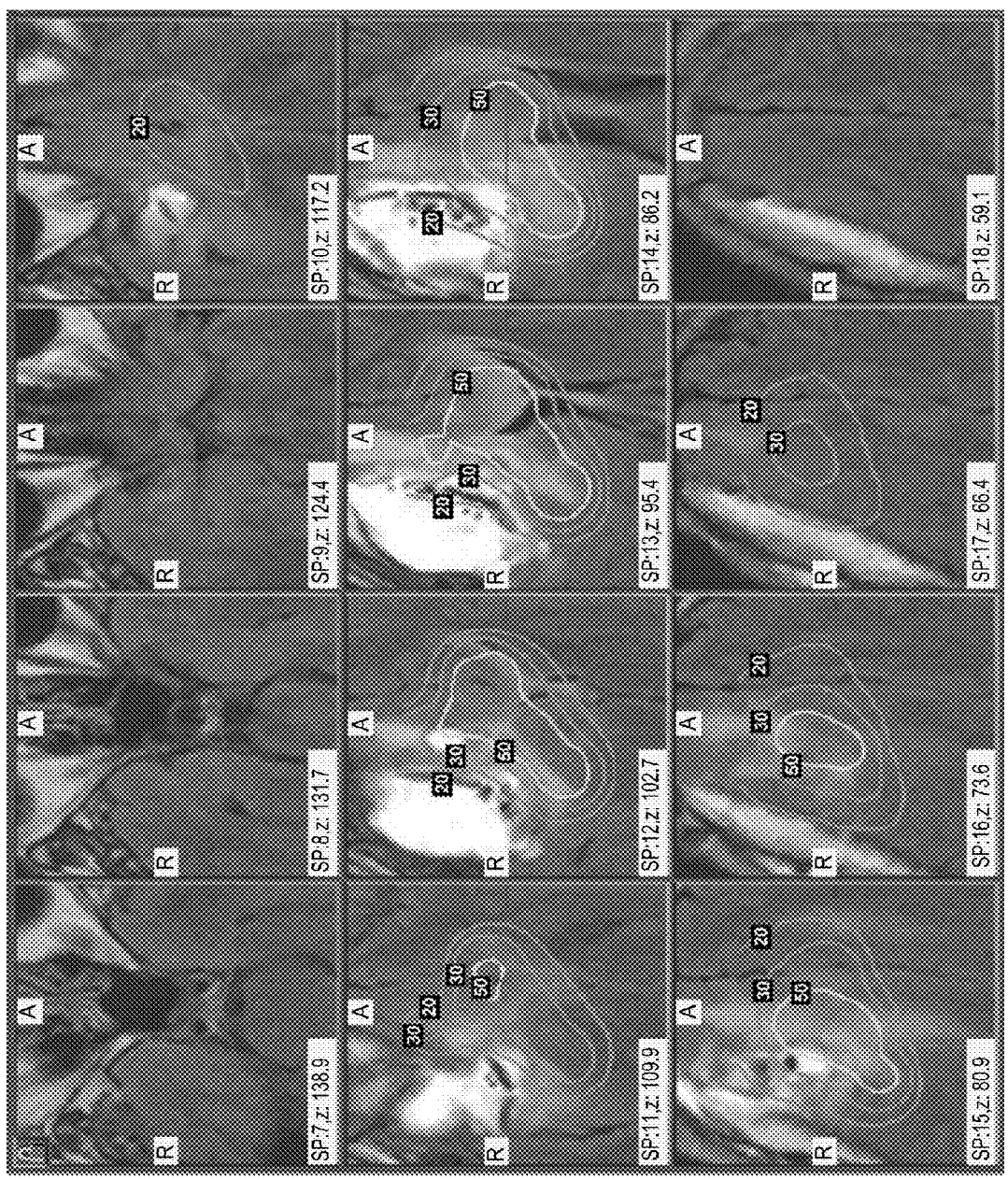
FIGS. 16 and 17 each show a series two dimensional tomographic images of a brain that collectively provide the viewer with a three dimensional representation of the treatment area.
Figure 17:
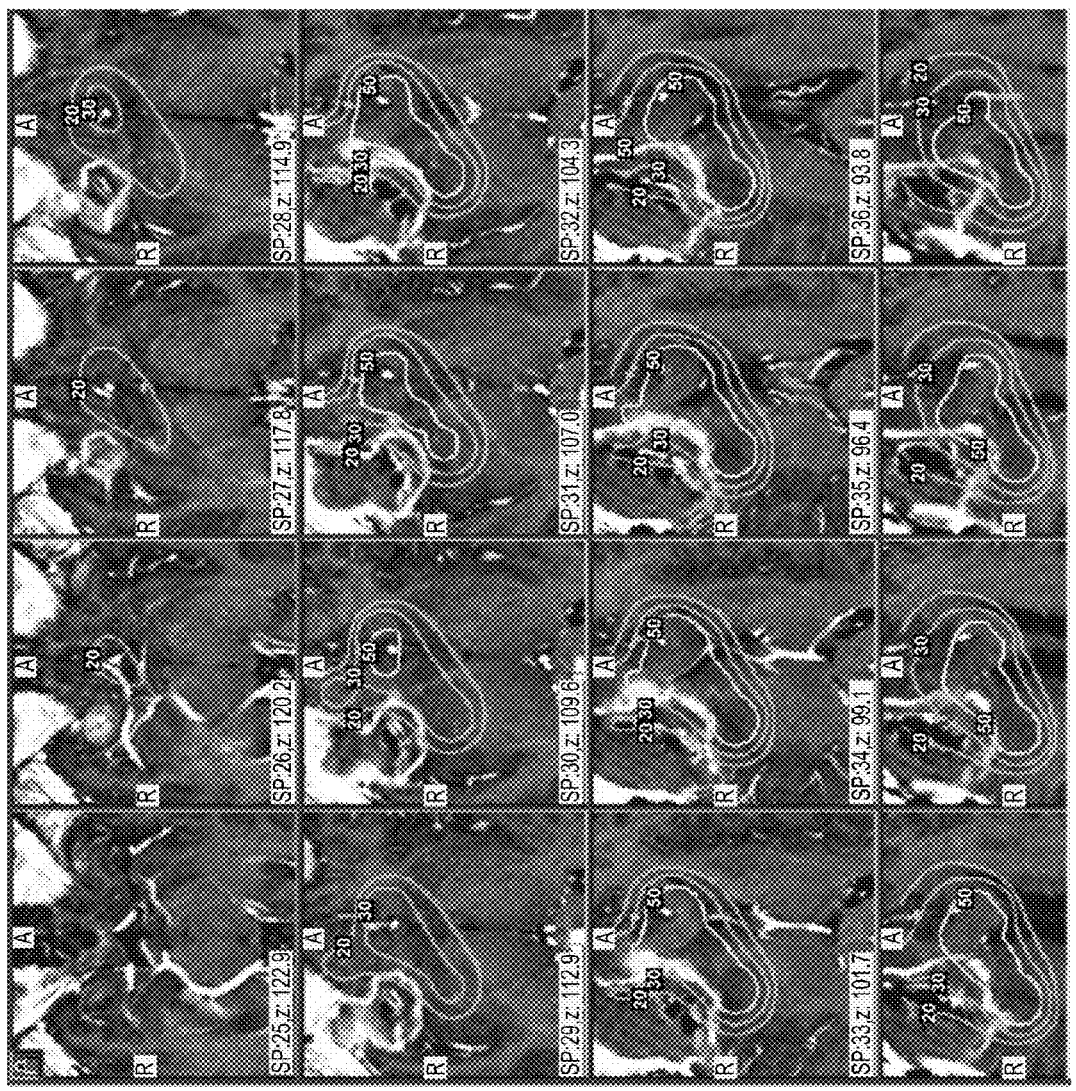

The treatment prescription module also can include one or more components related to the strength and profile of radiation to be applied at the remote region. In some embodiments, the dosage is defined to be at least an amount capable of providing an effective cancer treatment to, for example, provide enhanced life expectancy. In some embodiments, dosage is determined with reference to a known dose/volume histogram, e.g., a Flickinger Curve. For example, the treatment prescription module can output commands for treatment devices to apply one isodose of radiation along one trajectory or region and another isodose of radiation along another trajectory or region. In this way dosage can be calibrated to the likelihood of tumor cell migration to a given area. Examples of such dosages and target volumes include 14 Gy at 50% at 21 cc volume and 15 Gy and 50% at 17 cc volume; however persons skilled in the art will recognize that there are a wide variety of possible treatment regimens. Some examples of target sites for such treatment are shown in FIGS. 9-17. FIGS. 9 through 15 show images of radiation treatment profiles superimposed on a two dimensional tomographic image of a brain. FIGS. 16 and 17 each show a series two dimensional tomographic images of a brain that collectively provide the viewer with a three dimensional representation of the treatment area.

In some embodiments, the kit can further comprise one or more treatment devices. Such treatment devices can take any suitable form. In some cases, the treatment device is configured to deliver an amount of radiation that will prevent or minimize propagation of cancer cells, such as from an area of concentration of such cells to a remote area. As described herein, such migration is believed to occur along anatomical structures of the brain that exhibit relatively low resistance to cell migration. Such structures include leading-edge pathways of preferred migration. In some embodiments, the device is configured to collect spectral data and/or image data useful for planning spectroscopic treatment by determining composition of brain tissue at specified regions or the entire brain and/or determining what regions of brain tissue contain cancer cells that are either migrating or likely to migrate. In some embodiments, the device is further configured to analyze spectral data and/or image data to identify paths along which cancer cells likely will migrate. In some embodiments, the device is configured to execute a series of commands to administer leading-edge surgery based on an output based on spectral data and/or image data. In some embodiments, the device includes a Gamma Knife, or similar apparatus capable of executing leading-edge radiosurgery.

A prescribed treatment profile, for example a trajectory to be traced by a Gamma Knife, can be determined either functionally or based on known effective trajectories. For example, in some embodiments, the trajectory traced by stereotactic instrument that is closest to a cancer cell bulk is traced along a tissue region that is separated from the bulk by a sufficient distance to ensure that any cancer cells have not migrated beyond that distance. As a result, the treatment will be directed to a region that is farther from the bulk of cancer cells than are cells that are migrating from the bulk. This approach would radiate tissue in front of the leading edge of spreading cells to provide an effective leading-edge treatment. Such a treatment can kill latent cancer cells in these areas and thus provide a life expectancy for the patient that is greater than a median life expectancy based on the status of the patient's cancer. In some embodiments, the separation between the trajectory and the bulk is based on experimental results. In some embodiments, the separation between the trajectory and the bulk is based on a patient's history. In some embodiments a trajectory is selected or predicted based on an algorithm. In some embodiments, the trajectory traced can describe a regular or an irregular shape having a minimum separation from a cancer cell bulk of up to but not greater than about 1 cm. In some embodiments, this separation is from about 0.10 to about 0.35 cm. In some embodiments, this separation is from about 0.45 to about 0.75 cm. In some embodiments, this separation is from 0.9 to about 1.0 centimeters away. In some embodiments this separation is from about 1.0 cm to about 1.5 cm. Several exemplary treatment profiles are illustrated in FIGS. 9 through 17; however, persons skilled in the art will recognize that a wide variety of treatment profiles are possible.

In some embodiments, multiple trajectories are traced up to but not greater than a distance from one another and/or from known-cancerous regions. In some embodiments, multiple trajectories are traced on regions predicted to provide effective cancer treatment. In some embodiments, these regions are predicted based on experimental results. In some embodiments these regions are predicted based on an algorithm. In some embodiments, these regions are determined with reference to a patient's history. In some embodiments, the trajectories traced can describe regular or irregular shapes and can be spaced from each other by a minimum separation of up to but not greater than about 1 cm. In some embodiments, this separation is from about 0.10 to about 0.35 cm. In some embodiments, this separation is from about 0.45 to about 0.75 centimeters. In some embodiments, this separation is from about 0.9 to about 1.0 centimeters. In some embodiments this separation is from about 1.0 centimeters to about 1.5 centimeters.

Some embodiments provide a method of planning one or multiple leading-edge GKRS treatments in whole and/or in part. Some embodiments provide a method of executing one or multiple leading-edge GKRS treatments in whole and/or in part. Some embodiments provide a method of determining the efficacy of one or multiple leading-edge GKRS treatments. Some embodiments provide a method of determining a follow-up plan for executing or suggesting subsequent GKRS treatments after an initial GKRS treatment or series of GKRS treatments.

In some embodiments, a method is provided for reducing the cost to treat primary brain tumors. In some embodiments, a method is provided for reducing the amount of radiation needed to enhance survival time after a leading-edge procedure, e.g., a GKRS procedure. In some embodiments, a method and/or kit is provided to reduce the amount of expertise and/or time-in-surgery necessary to successfully treat a patient with a leading-edge procedure, e.g., a GKRS procedure.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In particular, while the present devices, systems, kits, and methods have been described in the context of particularly preferred embodiments, the skilled artisan will appreciate, in view of the present disclosure, that certain advantages, features and aspects of the system may be realized in a variety of other applications. Additionally, it is contemplated that various aspects and features of the invention described can be practiced separately, combined together, or substituted for one another, and that a variety of combination and subcombinations of the features and aspects can be made and still fall within the scope of the invention. Thus, it is intended that the scope of the present invention herein disclosed should not be limited by the particular disclosed embodiments described above.

What is claimed is:

1. A method for treating a cancerous tumor in a brain, the method comprising:
   identifying a bulk of the tumor or a nidus;
   predicting regions of likely cancer-cell migration based at least in part on patient population data corresponding to regions of likely or demonstrated cancer-cell migration in a patient population, wherein predicting the regions of likely cancer-cell migration comprises analyzing a location of the bulk of tumor or the nidus;
   imaging the brain to determine whether cancer cells have already migrated to the predicted regions;
   tracing a trajectory along a tissue region that is separated from the bulk of the tumor or the nidus by a sufficient distance to ensure that cancer cells have not spread beyond that distance, the trajectory being spaced apart from the bulk of the tumor or the nidus by a minimum separation;
   selectively treating likely healthy white matter pathways in the regions of likely cancer-cell migration using a stereotactic radiosurgery surgical apparatus to provide radiation treatment to tissue residing beyond the spreading cancer cells, wherein the white matter pathways selected for treatment are determined at least in part by the location of the bulk of tumor or the nidus.

2. A computer-implemented method of determining a target region for treating a cancerous tumor in a brain using one or more computer processors configured to execute the steps, the method comprising:
   distinguishing areas of non-cancerous tissue from areas of cancerous tissue;
   identifying a location of a bulk of the tumor or a nidus;
   predicting areas of likely cancer-cell migration lying at or beyond an outermost portion of the bulk of the tumor or the nidus and along a white matter pathway based at least in part on the location of the bulk of the tumor or the nidus and patient population data corresponding to regions of likely or demonstrated cancer-cell migration in a patient population;
   imaging the brain to determine whether cancer cells have already migrated to the predicted areas;
   tracing a trajectory along a tissue region that is separated from the outermost portion of the nidus by a sufficient distance to ensure that cancer cells have not spread beyond that distance, the trajectory being spaced apart from the bulk of the tumor or the nidus by a minimum separation; and
   treating a likely healthy region of the white matter pathway beyond the spreading cancer cells using a stereotactic radiosurgery surgical apparatus to prevent migration of cancer cells.

3. The method of claim 2, wherein distinguishing areas of non-cancerous tissue from areas of cancerous tissue comprises using Fluid-Attenuated Inversion-Recovery.

4. The method of claim 2, wherein establishing areas of noncancerous tissue from areas of cancerous tissue comprises using magnetic resonance spectroscopy.

5. The method of claim 2, wherein distinguishing areas of non-cancerous tissue from areas of cancerous tissue comprises using Fluid-Attenuated Inversion-Recovery and establishing areas of noncancerous tissue from areas of cancerous tissue comprises using magnetic resonance spectroscopy.

6. A computer-implemented method of treating cancer in brain tissue using one or more computer processors configured to execute the steps, the method comprising:
   locating a bulk of the tumor or a nidus of cancer in the brain tissue;
   locating remote cancer cells disposed outside an outer extent of the nidus;
   treating the remote cancer cells to minimize a spread of the cancer;
   predicting a likely white matter pathway along which cells could migrate from the bulk of the tumor or the nidus based at least in part on the location of the bulk of the tissue or the nidus and patient population data corresponding to regions of likely or demonstrated cancer-cell migration in a patient population;
   imaging the brain to determine whether cancer cells have already migrated along the likely white matter pathway;
   tracing a trajectory along a tissue region that is separated from the outer extent of the nidus by a sufficient distance to ensure that cancer cells have not spread beyond that distance, the trajectory being spaced apart from the bulk of the tumor or the nidus by a minimum separation; and
   treating a likely healthy region of the likely white matter pathway beyond the spreading cancer cells with radiation.

7. The method of claim 6, wherein the radiation is delivered using a stereotactic surgical instrument.

8. The method of claim 6, wherein the remote cancer cells are located using Fluid-Attenuated Inversion-Recovery data.

9. The method of claim 6, wherein the pathway of migration is determined using magnetic resonance spectroscopy.

10. A system for surgical planning comprising:
    a non-transitory computer-readable storage medium, having stored thereon a plurality of executable software modules;
    one or more computing devices including a processor, the one or more computing devices configured to at least:
    control an imaging device adapted to collect data useful in distinguishing areas of non-cancerous tissue from areas of cancerous tissue;

predicting a likely pathway of cancer cell migration along an origin lying at or beyond an outmost portion of a bulk of tumor or a nidus and along a white matter pathway based at least in part on the location of the bulk of tumor or the nidus and patient population data corresponding to regions of likely or demonstrated cancer-cell migration in a patient population;

imaging the brain to determine whether cancer cells have already migrated along the likely pathway;

tracing a trajectory along a tissue region that is separated from the outermost portion of the bulk of the tumor or the nidus by a sufficient distance to ensure that cancer cells have not spread beyond that distance, the trajectory being spaced apart from the bulk of the tumor or the nidus by a minimum separation; and treating a likely healthy region of the likely pathway using a stereotactic radiosurgery surgical apparatus to provide radiation treatment beyond the spreading cancer cells to prevent cancer cell migration.

11. A system for stereotactic surgery for administering therapy to areas of brain tissue comprising likely path way of malignant cell migration, the system comprising one or more computing devices and a non-transitory computer-readable storage medium loaded with an algorithm for directing at least one medical instrument to:

locate area comprising an outermost extent of a bulk of tumor or a malignant nidus based on a digital image of a tissue mass containing the bulk of tumor or the nidus;

locate areas of malignant cells outside the outermost extent of the bulk of tumor or the malignant nidus based on the digital image of the tissue mass;

predicting a likely pathway along a white matter pathway which malignant cells will migrate based at least in part on patient population data that identifies regions of likely or demonstrated cancer-cell migration in a patient population and the location of the bulk of the tumor or the nidus;

imaging the brain to determine whether cancer cells have already migrated along the likely pathway;

tracing a trajectory along a tissue region that is separated from the outermost extent of the bulk of the tumor or the malignant nidus by a sufficient distance to ensure that cancer cells have not spread beyond that distance, the trajectory being spaced apart from the bulk of tumor or nidus by a minimum separation; and treating a likely healthy region of the likely pathway to provide radiation treatment beyond the spreading cancer cells.

12. The computer-implemented system of claim 11, wherein the algorithm is further capable of instructing at least one medical instrument to treat at least one of the located areas with a dose of radiation from a stereotactic surgical instrument.

13. The computer-implemented system of claim 11, wherein predicting the likely pathway is further based at least in part on individual patient data that identifies regions of likely or demonstrated cancer-cell migration in an individual patient.

14. The computer-implemented system of claim 11, wherein the algorithm is further capable of comparing data obtained from the digital image of the tissue that identifies regions of likely or demonstrated cancer-cell migration to data corresponding to regions of likely or demonstrated cancer-cell migration in the population and outputs a suggested region or regions of tissue to treat with radiation therapy based on treatment efficacy data corresponding to radiation treatments administered to the population.

* * * * *

UNITED STATES PATENT AND TRADEMARK OFFICE
CERTIFICATE OF CORRECTION

PATENT NO. : 9,198,597 B2
APPLICATION NO. : 12/471294
DATED : December 1, 2015
INVENTOR(S) : Christopher Duma Page 1 of 1

It is certified that error appears in the above-identified patent and that said Letters Patent is hereby corrected as shown below:

Specification

In column 1 at line 13, Change "oliodendrocytes." to --oligodendrocytes.--.

Claims

In column 12 at line 15, In claim 12, change "The computer-implemented system of claim 11," to --The system of claim 11,--.

In column 12 at line 20, In claim 13, change "The computer-implemented system of claim 11," to --The system of claim 11,--.

In column 12 at line 25, In claim 14, change "The computer-implemented system of claim 11," to --The system of claim 11,--.

Signed and Sealed this
Twelfth Day of July, 2016

Michelle K. Lee
*Director of the United States Patent and Trademark Office*